(12) United States Patent
Magyar et al.

(10) Patent No.: US 12,398,174 B2
(45) Date of Patent: Aug. 26, 2025

(54) OPTICALLY VERIFIED POLYMER SYNTHESIS

(71) Applicant: The Charles Stark Draper Laboratory, Inc., Cambridge, MA (US)

(72) Inventors: Andrew P. Magyar, Acton, MA (US); Melissa M. Sprachman, Somerville, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 18/453,623

(22) Filed: Aug. 22, 2023

(65) Prior Publication Data
US 2023/0391819 A1    Dec. 7, 2023

Related U.S. Application Data

(62) Division of application No. 16/473,462, filed as application No. PCT/US2018/012598 on Jan. 5, 2018, now Pat. No. 11,773,133.

(60) Provisional application No. 62/447,960, filed on Jan. 19, 2017, provisional application No. 62/443,149, filed on Jan. 6, 2017.

(51) Int. Cl.
| | |
|---|---|
| C12Q 1/68 | (2018.01) |
| C07F 7/08 | (2006.01) |
| C07K 1/08 | (2006.01) |
| C07K 14/00 | (2006.01) |
| C09K 11/06 | (2006.01) |

(52) U.S. Cl.
CPC ............ C07K 1/088 (2013.01); C07F 7/08 (2013.01); C07K 14/003 (2013.01); C09K 11/06 (2013.01); C12Q 1/68 (2013.01); *C09K 2211/14* (2013.01); *C12Q 2563/107* (2013.01)

(58) Field of Classification Search
CPC ........ C07K 1/08; C07K 1/088; C07K 14/003; C12Q 1/68; C09K 11/06; C09K 2211/14
See application file for complete search history.

(56) References Cited

U.S. PATENT DOCUMENTS 5,539,082 A * 7/1996 Nielsen .................. A61P 31/00
544/242
11,773,133 B2  10/2023 Magyar et al.
2002/0015961 A1  2/2002 Kwiatkowski
2009/0137419 A1  5/2009 Dower et al.
2009/0233302 A1  9/2009 Wegener et al.
2013/0244884 A1  9/2013 Jacobson et al.
2016/0272623 A1  9/2016 Johnson et al.

FOREIGN PATENT DOCUMENTS

| WO | WO 00/53805 | 9/2000 |
|---|---|---|
| WO | WO 2004/022578 A2 | 3/2004 |
| WO | WO 2008/042067 A2 | 4/2008 |
| WO | WO 2012/012756 A1 | 1/2012 |
| WO | WO 2017/156218 A1 | 9/2017 |

OTHER PUBLICATIONS

Banerjee, S.R. et al., "Site directed malimide bifunctional chelators for the M(CO)3+ core (m=99mTc, Re)," Communication, 1784-1786 (2005).
Barbeyron, R. et al., "Synthesis of 3'-deoxy-3'-iminodiacetic acid and 3'-deoxy-3'-aminodiethanol thymidine analogues and NMR study of their complexation with boronic acids," Tetrahedron, 73: 2468-2475 (2017).
Chawla, R. et al., "Preparation of 1,1,3,3-Tetraisopropyl-1,3-Dichlorodisiloxane and Triisopropylchlorosilane," Synthetic Communications, 29(20): 3499-3501 (1999).
Colgin, N. et al., "Synthesis and properties of MIDA boronate containing aromatic amino acids: New peptide building blocks," Organic & Biomolecular Chemistry, 9: 1864-1870 (2011).
Gillis, E.P., et al., "Iterative Cross-Couplng with MIDA Boronates: Towards a General Platform for Small Molecule Synthesis," 42(1): 17-27 (2009).
Grob, J.E., et al., "Regioselective Synthesis and Slow-Release Suzuki-Miyaura Cross-Coupling of MIDA Boronate-Functionalized Isoxazoles and Triazoles," JOC, 75: 10241-10248 (2011).
Guo, X. et al., "New and One Pot Chemoslective Synthesis of Nucleoside 5'-H-Phosphonate Diesters," Nucleosides, Nucleotides, and Nucleic Acids, 24(9): 1325-1331 (2005).
International Search Report and Written Opinion of the International Searching Authority, mailed on May 3, 2018, from International Application No. PCT/US2018/012598, filed on Jan. 5, 2018. 24 pages.
Maeda, H. et al., "Absorption and Fluorescence Spectroscopic Properties of 1- and 1,4-Silyl-Substituted Naphthalene Derivatives," Molecules, 17: 5108-5125 (2012).
Masuda, M. et al., "Synthesis of a Versatile Probe for Analysis of Cytoplasmic Peptide-N-Glycanase," Journal of the Chinese Chemical Society, 59: 269-272 (2012).
Niu, J. et al., "Enzyme-free translation of DNA into sequence-defined synthetic polymers structurally unrelated to nucleic acids," Nature Chemistry, 5: 282-292 (2013).

(Continued)

*Primary Examiner* — Jezia Riley
(74) *Attorney, Agent, or Firm* — Wolf, Greenfield & Sacks, P.C.

(57) ABSTRACT

Compositions and methods for optically-verified, sequence-controlled polymer synthesis are described.

13 Claims, 7 Drawing Sheets

(56) References Cited

OTHER PUBLICATIONS

Osterman, H.L. et al., "White Paper: Near-Infrared Fluorescence Imaging: Seeing Beyond the Visible with IRDye® Infrared Dyes," LI-COR Biosciences, 1-18 (2012).
Pothukanuri, S. et al., "Expanding the Scope and Orthogonality of PNA Synthesis," Eur. J. Org. Chem., 3141-3148 (2008).
Robertson, J. et al., "Ene cyclisations of α-(prenyl)dialkylsilyloxy aldehydes: formation and oxidative cleavage of oxasilacyclohexanols," The Royal Society of Chemistry, 1: 3758-3767 (2003).
Scott, J.P. et al., Mitsunobu Inversion of a Secondary Alcohol with Diphenylphosphoryl azide. Application to the Enantioselective Multikilogram Synthesis of a HCV Polymerase Inhibitor,: Org. Process Res. Dev., 15: 1116-1123 (2011).
International Preliminary Report on Patentability, mailed on Jul. 18, 2019, from International Application No. PCT/US2018/012598, filed on Jan. 5, 2018. 15 pages.

* cited by examiner

OPTICALLY VERIFIED POLYMER SYNTHESIS

RELATED APPLICATIONS

This application is a Divisional of U.S. application Ser. No. 16/473,462, filed on Jun. 25, 2019, now U.S. Publication No. US 2019/0322699, published on Oct. 24, 2019, which is a § 371 National Phase Application of International Application No. PCT/US2018/012598, filed on Jan. 5, 2018, now International Publication No. WO 2018/129328, published on Jul. 12, 2018, which International Application claims the benefit under 35 USC 119(e) of U.S. Provisional Application No. 62/443,149 filed on Jan. 6, 2017, and U.S. Provisional Application No. 62/447,960, filed on Jan. 19, 2017, all of the teachings of which are incorporated herein by reference in their entirety.

BACKGROUND OF THE INVENTION

Demands for functional materials engineered at the molecular level are leading researchers to develop new methodologies for the sequence-controlled synthesis of polymers. Biopolymers, such as proteins and nucleic acids, can have sequences that are hundreds to millions of units long, however currently the controlled synthesis of non-biological polymers has been limited to 10s of repeating units. These syntheses are hampered by premature termination and poor synthetic yields. In biological systems, enzymes and other biological machinery actively monitor and repair damage and errors during biopolymer synthesis. To overcome the limitations of sequence-controlled synthesis there is a need for new synthetic methods that enable in situ monitoring of synthetic efficiency, kinetics, and structural characteristics of the extending polymer chain.

SUMMARY OF THE INVENTION

The present invention encompasses compositions and methods for sequence-controlled polymer chain synthesis. The invention provides methods and compositions that enable the synthesis of polymers/oligomers having a specified sequence while providing detectable (e.g., optical verification such as detecting a fluorescent label) characterization of the product at each synthetic step. Specifically, the invention provides the ability to fluorescently validate the addition of each monomeric building block to the end of a polymer chain as it is being extended. The polymer chain sequence is determined prior to the start of the synthetic process.

As described herein, the compositions encompassed by the present invention comprise monomer units that are suitable for use in the polymer chain synthesis methods described herein. In particular, a monomer unit will comprise a bifunctional building block molecule/component (e.g., a nucleotide either naturally-occurring or non-naturally-occurring) with one, or more, protecting groups (also referred to herein as blocking groups). As described herein, a blocking group can be attached to the building block molecule at a specified end. The blocking groups are removable/cleavable using standard chemical conditions and reagents, which importantly, are orthogonal to the chemistry used for the sequential addition of monomer units required to extend the polymer/oligomer chain length. For example, an amino acid (naturally-occurring or non-naturally-occurring) can comprise a protecting or blocking group such as fluorenylmethyloxycarbonyl chloride (Fmoc) groups on the alpha nitrogen where amide bond couplings are executed by coupling between a free acid on the building block or an unblocked amine on the growing polymer chain. After addition, the Fmoc group is cleaved to unmask an amine that will couple with the free acid of the next N-Fmoc protected building block.

Alternatively, a monomer unit comprising the bifunctional building block (a first molecular moiety/entity or component) can comprise a second, additional molecular moiety/entity/component (e.g., forming a monomer complex). Such a monomer unit is also referred to herein as a macrocycle, or a macrocycle monomer unit. For example, a monomer unit comprising the desired building block (e.g., a non-naturally-occurring nucleotide or other naturally-occurring or non-naturally occurring biomolecule) can be linked or chemically coupled to a second biomolecule, such as a peptide nucleic acid (PNA) of a specific sequence. The linkage can be a cleavable linkage, such as a disulfide bond. As used herein, the term "monomer unit" comprises both alternative monomer unit embodiments described above.

The monomer unit blocking groups can be detectably labeled with a suitable label, for example a fluorophore (fluorescent label) detectable in the UV or visible spectrum (e.g., carbocyanime dyes or Alexa Fluor®) or in the near infrared or infrared spectrum (e.g., LiCor IRDye®). The detectable label can comprise a cleavable or flexible linker. In one embodiment of the present invention, the monomer unit comprises an N-methyliminodiacetic acid (MIDA) boronate analog, and in a particular embodiment, in the MIDA-boronate analog the methyl is group is substituted with a fluorophore linker moiety. In another embodiment of the present invention, the monomer unit comprises a fluorescent silyl group, and more particularly is an analog of triisopropyl silyl chloride. In another embodiment, such as in the macrocycle monomer unit described above, the second molecule of the unit can comprise the detectable label, for example the PNA can be detectably labeled.

The monomer units described herein can be used in methods of sequence-specific polymer/oligomer synthesis. In one embodiment the synthesis can be integrated with a microfluidic device such as that described in PCT/US2017/0333770 and PCT/US2017/033772, the teachings of which are herein incorporated by reference. Nanophotonic detection devices are also suitable for use in the methods of the present invention.

In general, the method comprises first immobilizing a polymer/oligo chain seed molecule on a surface. The surface can be a solid surface or support such as polymer, glass, silicon, or metal substrate, a bead, a gel, or any other support compatible with the methods described herein. The immobilization of the seed molecule can be optically verified, and in particular, verified by fluorescent means known to those of skill in the art. After immobilization, the support with the seed molecule is contacted with a detectably-labeled monomer unit under suitable reactive conditions. The detectable label moiety can be a cleavable moiety. The monomer unit (as described above) comprises a building block of interest (e.g., the desired nucleotide). The contact is made under reactive conditions (e.g., temperature and time) suitable for the addition (e.g., chemical addition or hybridization) of the monomer unit to the immobilized seed molecule, including the reagents (e.g., buffers, washes) required for the addition reaction (as used herein, the term "addition" encompasses either chemical addition to the reactive end of the immobilized seed molecule or binding to the seed molecule by hybridization). Such conditions can be determined by those of skill in the art. After the addition reaction is complete, the excess monomer units (those units not added or hybridized to the seed molecule) removed, typically by suitable wash cycles. After the removal step, specific addition of the monomer unit is verified by detecting the presence or absence of the detectable label, wherein the detectable presence of the label indicates specific addition of the desired monomer unit. After the verification step, the detectable label moiety can be removed or cleaved from the monomer unit by methods known to those of skill. The steps described above are sequentially repeated until the desired sequence-controlled polymer chain comprising the specific building blocks of interest is completely synthesized.

In particular, one embodiment for verifiable polymer chain synthesis encompasses template-free iterative chemistries, while another embodiment encompasses a DNA-templated oligomer synthesis The template-free method of synthesis described herein encompasses monomer units with a set of compatible monomer chemistries such as MIDA boronates, which can be iteratively assembled through Suzuki-Miyaura cross-coupling reactions. To enable fluorescent validation of each step, a fluorescent "blocking" group is added to the boronic acid preventing reaction at the "reactive" site. Alternative monomer chemistries described herein include iterative click chemistries and iterative Sonagashira couplings. To synthesize a sequence controlled polymer chain a seed molecule is immobilized on a surface, which can be polymer, glass, silicon, or metal substrate, a bead, a gel, or other solid support. The immobilization of this seed molecule can optionally be validated fluorescently. A monomer unit comprising a building block of interest (e.g., the desired nucleotide) is added to (e.g., chemically coupled to) the immobilized molecule using standard chemical techniques. Excess monomer and reagents are then flushed away. The successful addition of a building block is fluorescently validated, and the fluorescent blocking group is then removed, thereby activating the molecule for the next iterative addition, and the process restarts until the completed sequence has been synthesized.

In the DNA-templated method for oligomer synthesis, monomer units are coupled to a peptide nucleic acid (PNA) through disulfide bonds to form the monomer unit complex or macrocycles as described above. (See for example Niu et al. [1]). To enable fluorescent validation, a fluorophore can either be covalently attached to the PNA or attached as a cleavable blocking group. For this synthetic method, the sequence of the oligomer is defined by a single stranded DNA molecule. Each monomer unit comprises a building block coupled to a PNA with a specific associated nucleic acid sequence, or codon, enabling them to be assembled through hybridization between the PNA molecules and the template DNA molecule. The building block/PNA complex is referred to herein as a "macrocycle". To synthesize a sequence controlled polymer chain, a seed ssDNA molecule that defines the desired oligomer sequence is immobilized on a surface, which could be a polymer, glass, silicon, or metal substrate, a bead, a gel, or other solid support. The immobilization of this seed molecule can optionally be validated fluorescently. The macrocycle corresponding to the first codon in the template DNA is introduced and hybridized on to the template. Excess monomer and reagents are flushed away, and the successful hybridization is fluorescently validated. The macrocycle corresponding to the next codon is introduced and hybridized on to the template. Excess monomer and reagents are flushed away, and the successful hybridization is fluorescently validated. If required, the fluorescent blocking group is removed thereby activating the macrocycle for coupling and the appropriate reagents for the coupling reaction between the two monomers are introduced. The process restarts and is repeated for each codon until the synthesis is completed. Upon completion of the synthesis, the disulfide linkages that connect the monomer unit to the template PNA are cleaved, releasing the completed oligomer from the template DNA/PNA strand.

Additionally, fluorescence resonance energy transfer between the terminal fluorophore and a fluorophore at a previous selected location within the polymer chain enables the measurement of distances between units within the polymer. (see FIG. 1). Characterizing the distance between two points of a polymer as it is being synthesized (e.g., as the polymer chain is extended or grows) can provide insights in to the changes in secondary structure of that polymer, from which one may be able to infer reasons for stalling or premature termination of synthesis. Determination of the distance between two points during synthesis can be achieved through the incorporation of a second marker fluorophore that is not coupled to the protecting group either in the seed molecule, the template strand, or as a pendant group off of a specified monomer. If the terminating fluorophore molecule and the marker fluorophore are selected so that one is a donor and the other an acceptor, thus enabling energy transfer between the two molecules. The efficiency of this energy transfer is inversely proportional to sixth power of the distance between the donor and acceptor and thus this energy transfer can be used to measure the distance between the donor and the acceptor molecule. This approach can be used in either of the methods described above by characterizing changes in lifetime of the fluorophore during the fluorescence verification step to quantify the energy transfer and thereby the distance between the two selected points in the polymer chain.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Copies of this patent or patent application publication with color drawings will be provided by the Office upon request. Of the drawings:

FIG. 4A shows an iterative cross-coupling strategy using click chemistry.

FIGS. 6 A and B: Example PNA macrocycles containing a fluorophore that can be used for DNA-templated polymer synthesis.

DETAILED DESCRIPTION OF THE PREFERRED EMBODIMENTS

Figure 1:
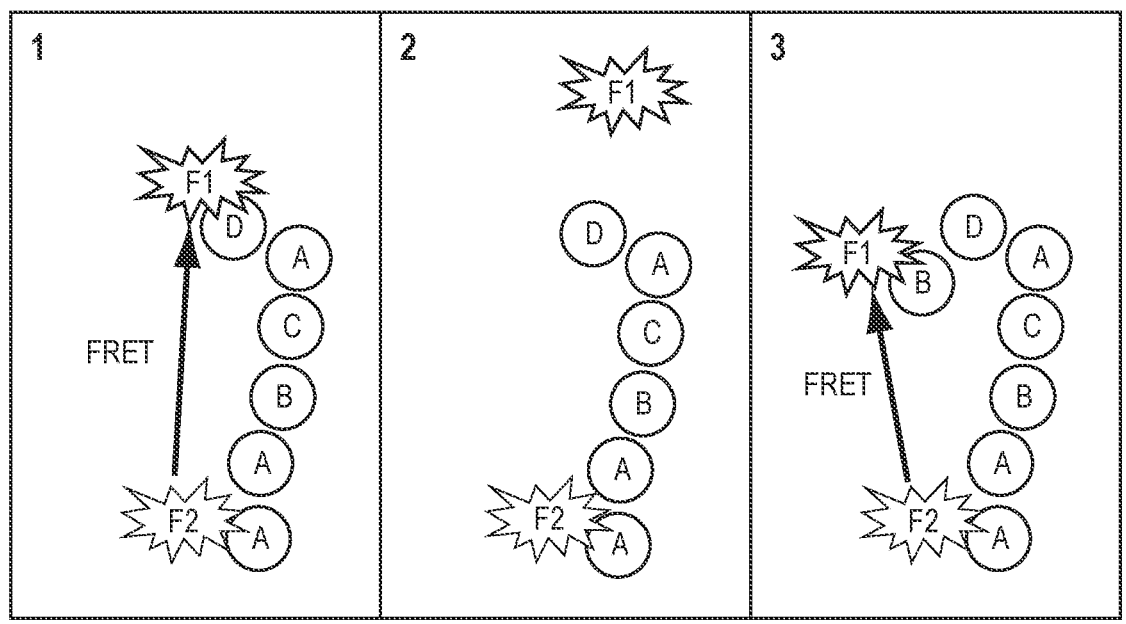
FIG. 1: A schematic representation of FRET between two fluorophores, one coupled to a fixed position in the molecular chain and one attached to the terminal unit, which can be used to measure changes in the distance between polymer units during synthesis.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Iterative Synthesis Chemistries
Immobilization of Seed Molecule

A "seed" molecule is immobilized on a substrate as described above. The chemistries for this immobilization may enable the later chemical removal of this seed molecule and the final oligomer chain. Methods for immobilization of the seed molecule can include, but are not limited to, acid-labile linkers (e.g. azidomethyl-methyl maleic anhydride, silyl ethers) or photocleavable linkers (e.g. orthonitrobenzyl alcohols). Upon completion of synthesis suitable linkers will be cleaved "on demand" by selective chemical, electrochemical, or photochemical methods that will not affect the stability of the grown oligomer chain (e.g., orthogonal chemistries).

Synthesis of a Fluorophore-Labeled MIDA Boronate

Figure 2:
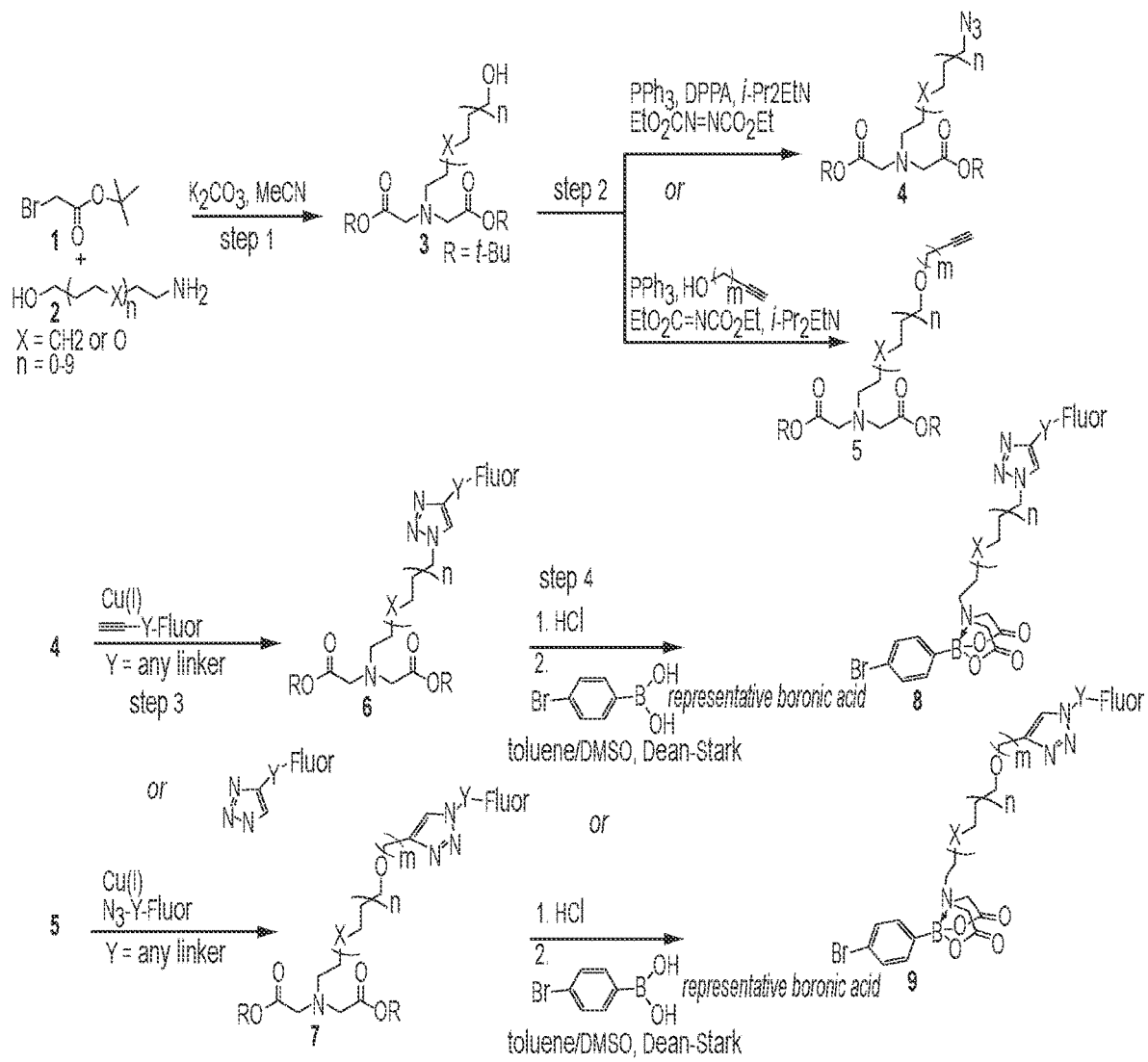
FIG. 2: A representative synthesis of a fluorophore-labeled MIDA-boronate analog for iterative synthesis.

The synthesis as shown in FIG. 2 allows for flexibility with linker selection for the nitrogen in the iminodiacetic acid ligand as well as fluorophore selection. MIDA (N-methyliminodiacetic acid) analogs where the methyl is replaced by a linker fluorophore could be constructed by alkylation of an amino alcohol 2 with tert-butyl bromoacetate 1 under established conditions. [2] The resulting free alcohol is either converted to an azide or alkyne-substituted ether using Mitsunobo conditions to afford compounds 4 or 5. [3] Compound 5 can also be formed by first converting compound 3 to the corresponding tosylate and then substituting with the alkynyl-alcohol in the presence of a base (e.g., sodium hydride). Cu-catalyzed click chemistry will then be used to install a fluorophore, yielding compounds 6 or 7. Many "clickable" fluorophores conjugated to either azides or alkynes are commercially available from companies such as Click Chemistry Tools or ThermoFisher Scientific. Finally, removal of the tert-butyl groups and boronic ester exchange with commercially available boronic acids will yield fluorophore-labeled MIDA boronate analogs 8 or 9 [4]. Alternatively, steps 3 and 4 could be reversed (generating the MIDA boronate analogs first, followed by click chemistry for fluorophore introduction). Click chemistry of MIDA boronates is known. [5]

Iterative Cross-Coupling with MIDA Boronate

Figure 3:
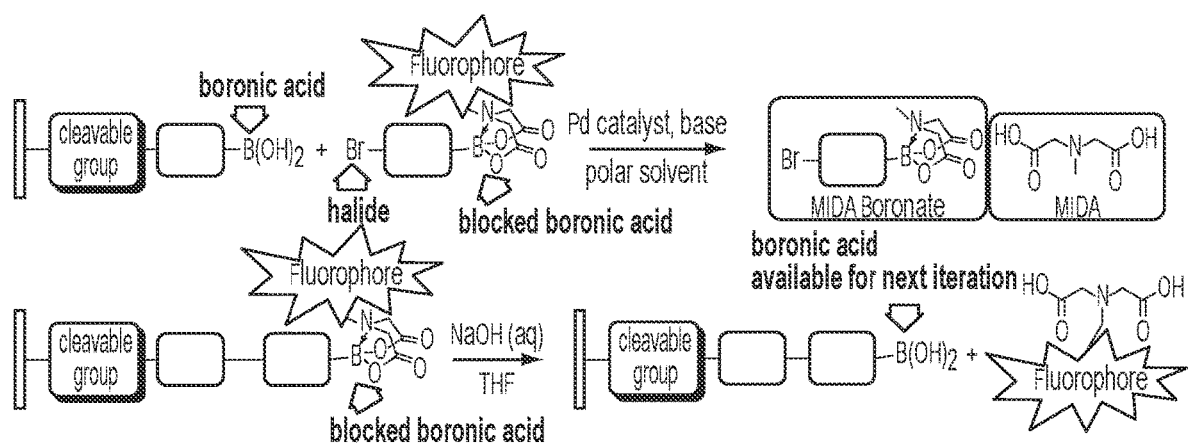
FIG. 3: An iterative cross-coupling strategy using MIDA boronates.

An immobilized molecule with a terminal boronic acid as shown in FIG. 3 is reacted with a MIDA boronate with a blocked boronic acid that has a pendant fluorophore on the blocking group. In the presence of a Pd catalyst, base, and polar solvent, the halide on the MIDA boronate reacts with the boronic acid through a Suzuki-Mayaura cross-coupling reaction to form a carbon-carbon bond. The addition can then be fluorescently verified, and then the fluorophore and the blocking group on the boronic acid removed by treatment with NaOH and THF, leaving a boronic acid group available for the subsequent addition.

Alternative Fluorophore-Labeled Building Blocks

Figure 4A:
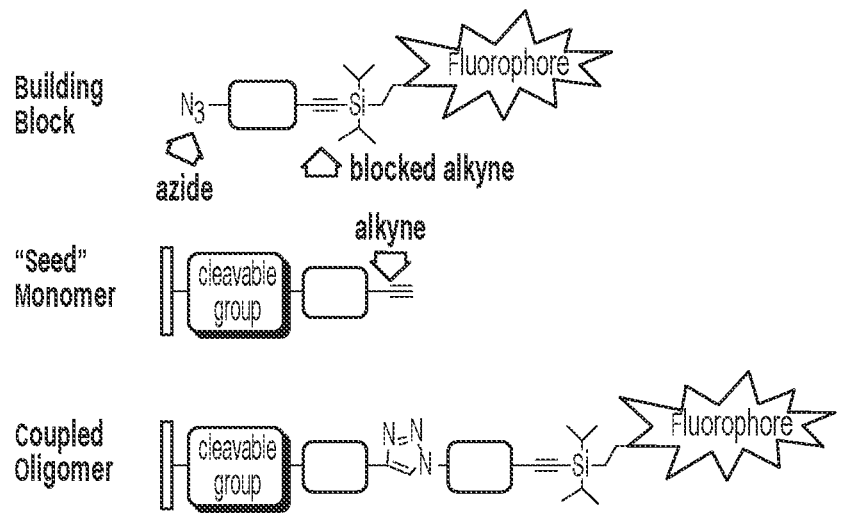
FIGS. 4A and B.
Figure 4B:
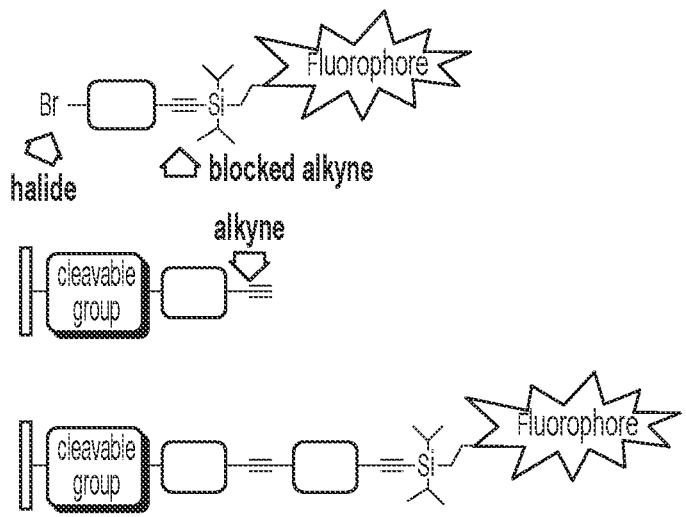
FIG. 4B shows an iterative cross-coupling strategy using Sonagashira couplings.

Other potential iterative chemistries would be an iterative click reaction wherein each step is blocked by capping the alkyne with a fluorescent silyl group. A similar concept could be applied to iterative Sonagashira chemistries. (See FIGS. 4A and B). Although the fluorescent silyl protecting group Bistert-butyl chloro(pyren-1-ylmethoxy)silane has been used, it has limitations in that the excitation/emission wavelengths are fixed and still in the far UV range (346/390 nm, respectively). [6]

Figure 5:
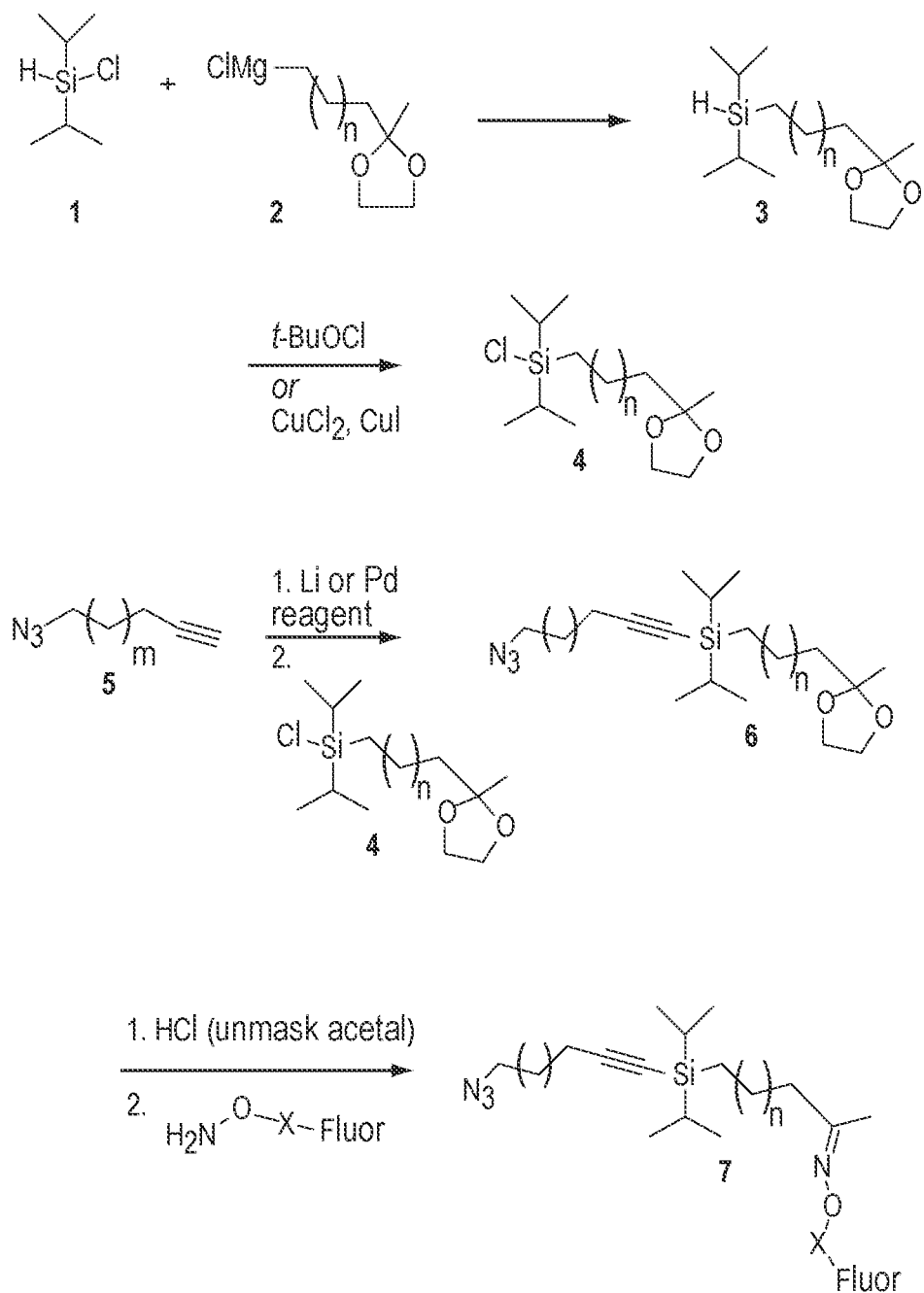
FIG. 5: A representative synthesis for a fluorescent analog of triisopropyl silyl chloride.

A fluorescent analog of triisopropyl silyl chloride, the synthesis for which is shown in FIG. 5, could be used with either an iterative click chemistry, Sonagashira chemistry, or the macrocycles. A silyl group with a handle for conjugation could be prepared by Grignard addition of a masked ketone (e.g., generic structure 2) to diisopropylchlorosilane 1. [7] Chlorination of the silylating agent could be carried out using a number of conditions known to those skilled in the art, an example being tert-butyl hypochlorite [8] or CuCl2/CuI [7]. The silyl chloride can added to an alkyne to generate the bifunctional building block by activation the terminal alkyne with an organometallic agent, such as a lithium reagent. Unmasking the ketone and forming the oxime through condensation with a hydroxylamine-conjugated fluorophore (commercially available from ThermoFisher Scientific) would yield the fluorescently tagged building block.

Alternative Iterative Cross-Coupling

An immobilized molecule with a terminal alkyne is reacted with a monomer containing an azide and a silyl-protected alkyne with a pendant fluorophore in the presence of a Cu catalyst. The addition can then be fluorescently verified and then the fluorophore and the silyl blocking group are removed through the introduction of fluoride ions, leaving an alkyne group available for the subsequent addition.

Alternatively, an immobilized molecule with a terminal alkyne is reacted with a monomer containing a halide and a silyl-protected alkyne with a pendant fluorophore in the presence of a Pd and a Cu catalyst through a Sonagashira coupling reaction. The addition can then be fluorescently verified and then the fluorophore and the silyl blocking group are removed through the introduction of fluoride ions, leaving an alkyne group available for the subsequent addition.

Templated Synthesis

Synthesis of Fluorescent Macrocycles

Figure 6A:
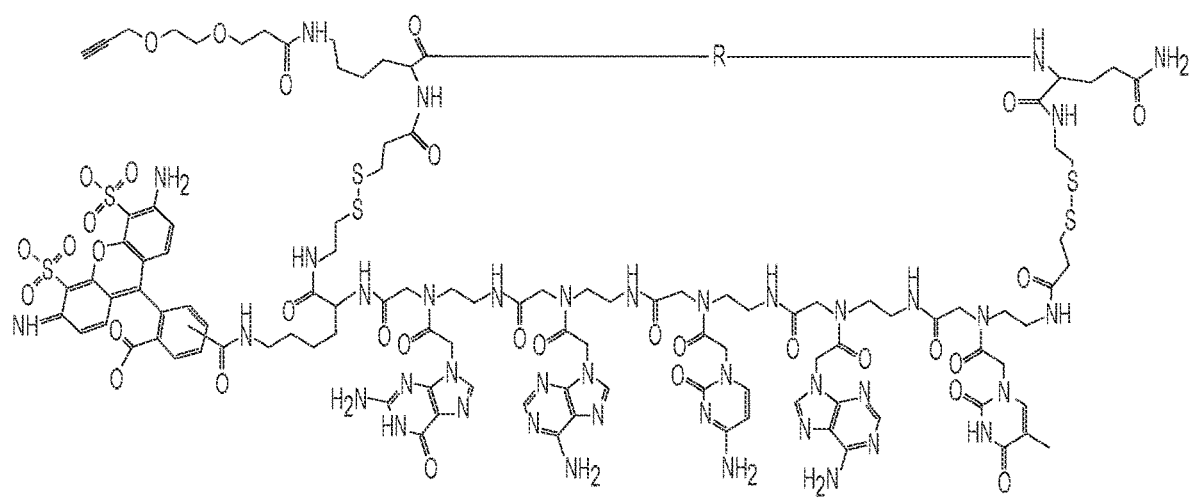
FIG. 6A shows a fluorophore labeled PNA.
Figure 6B:
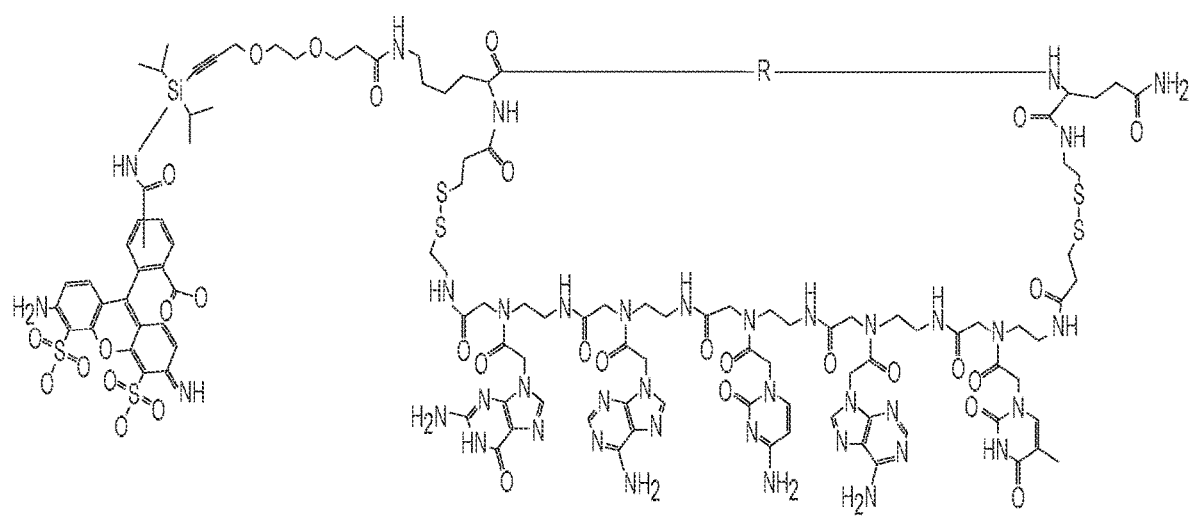
FIG. 6B shows a fluorophore labeled blocking group.

The macrocycles containing the polymer building block and the PNA can be synthesized as described in [1]. The silyl/fluorophore protected alkyne can be synthesized as shown in FIG. 5. For the incorporation of a non-terminating fluorophore, a fluorophore containing amino acid can be incorporated during the synthesis of the PNA complex, prior to formation of the macrocycle (FIGS. 6A and B).

REFERENCES

[1] *Nature Chemistry* 2013, 5, 282-292.
[2] For an example, see Tetrahedron 2017 73, 2468.
[3] For Mitsunobo conditions to install azides, see *Org. Process Res. Dev.* 2011, 15, 1116; for Mitsunobo chemistry on iminodiacetic acid substrates, see *Chem. Commun.* 2005, 13, 1784.
[4] Example of using halide-substituted boronic acids to synthesize MIDA boronates: *Aldrichimica Acta* 2009, 42, 17-27
[5] Journal of Organic Chemistry 2011, 76, 10241-10248.
[6] Nucleotides & Nucleosides, and Nucleic Acids, 2005, 24, 1345
[7] Organic & Biomolecular Chemistry 2003, 1, 3758.
[8] Synthetic Communications 1999, 29, 3499.

The entire contents of the publications, patents and patent applications described herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims

What is claimed is:

1. A monomer unit,
    comprising a bifunctional building block comprising a removable, fluorescently-labeled protecting group;
    wherein the protecting group comprises a boronate analog, a silyl group, or a silyl analog; and
    wherein the bifunctional building block is coupled to a peptide nucleic acid (PNA) through disulfide bonds to form a macrocycle.

2. The monomer unit of claim 1, wherein the PNA is fluorescently-labeled.

3. The monomer unit of claim 1, wherein the protecting group comprises a fluorescent silyl group.

4. The monomer unit of claim 1, wherein the protecting group comprises an analog of triisopropyl silyl chloride.

5. A method of synthesizing a polymer of pre-determined sequence, the method comprising the steps of:
    a) contacting a polymer seed molecule immobilized on a solid support with a monomer unit of claim 1 comprising a bifunctional building block comprising a removable, fluorescently-labeled protecting group, under conditions and with reagents suitable for addition of the monomer unit/bifunctional building block to the immobilized seed molecule or an immobilized seed molecule extended by one or more monomer units/bifunctional building blocks;
    b) removing excess monomer units and reagents not added to the immobilized seed molecule or the immobilized seed molecule extended by one or more monomer units/bifunctional building blocks;
    c) verifying addition of the monomer unit/bifunctional building block by detecting the presence of the fluorescently-labeled protecting group, thereby extending the polymer by one monomer unit/bifunctional building block;
    d) removing the fluorescently-labeled protecting group of the monomer unit added to the immobilized seed molecule or the immobilized seed molecule extended by one or more monomer units/bifunctional building blocks; and
repeating steps a) through d) to synthesize the polymer.

6. A monomer unit comprising a bifunctional building block coupled to a peptide nucleic acid (PNA) through disulfide bonds to form a macrocycle,
    wherein the macrocycle is fluorescently-labeled,
    and optionally wherein the bifunctional building block comprises a removable protecting group, and the protecting group comprises a boronate analog, a silyl group, or a silyl analog.

7. A method of DNA-templated synthesis of a polymer of pre-determined sequence, the method comprising the steps of:
    a) immobilizing a single-stranded DNA seed molecule on a solid support;
    b) optionally verifying immobilization of the seed molecule;
    c) hybridizing the monomer unit of claim 6 to the immobilized seed molecule under conditions and with reagents suitable for the hybridization of the monomer unit to the immobilized seed molecule, wherein the monomer unit comprises a bifunctional building block coupled to a peptide nucleic acid (PNA) to form a macrocycle, and wherein the macrocycle is fluorescently-labeled;
    d) removing excess monomer units not hybridized to the immobilized seed molecule;
    e) verifying the hybridization of the monomer unit by detecting the presence of the fluorescently-labeled macrocycle; and
    f) repeating steps c) through e) to obtain the polymer of pre-determined sequence.

8. The method of claim 7, further comprising as step (g) cleaving the disulfide bonds coupling the bifunctional building blocks to the PNA, thereby releasing the sequence-specific polymer chain from the immobilized seed molecule.

9. The monomer unit of claim 6, wherein the PNA is fluorescently-labeled.

10. The monomer unit of claim 6, wherein the bifunctional building block is fluorescently labeled.

11. The monomer unit of claim 10, wherein the bifunctional building block comprises a removable protecting group.

12. The monomer unit of claim 11, wherein the removable protecting group is fluorescently labeled.

13. The monomer unit of claim 1, wherein the protecting group comprises a boronate analog.

* * * * *